(12) United States Patent
Kokish

(10) Patent No.: US 6,544,223 B1
(45) Date of Patent: Apr. 8, 2003

(54) BALLOON CATHETER FOR DELIVERING THERAPEUTIC AGENTS

(75) Inventor: Lyudmila Kokish, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/755,386

(22) Filed: Jan. 5, 2001

(51) Int. Cl.[7] ................. A61M 29/00; A61M 31/00; B05D 3/00; B01J 13/00

(52) U.S. Cl. ............... 604/103.01; 604/96.01; 604/97.01; 604/103.02; 604/103.06; 427/2.1; 427/2.31

(58) Field of Search ............ 604/96.01, 97.01, 604/103.01, 103.02, 103.06; 427/2.1, 2.31

(56) References Cited

U.S. PATENT DOCUMENTS

| | | | |
|---|---|---|---|
| 4,871,542 A | * 10/1989 | Vilhardt | 424/423 |
| 5,087,244 A | * 2/1992 | Wolinsky et al. | 604/96 |
| 5,213,576 A | 5/1993 | Abiuso et al. | 604/96 |
| 5,229,045 A | 7/1993 | Soldani | 264/41 |
| 5,318,531 A | * 6/1994 | Leone | 604/96 |
| 5,405,472 A | 4/1995 | Leone | 156/218 |
| 5,611,775 A | 3/1997 | Machold et al. | 604/53 |
| 5,624,411 A | 4/1997 | Tuch | 604/265 |
| 5,679,400 A | 10/1997 | Tuch | 427/2.14 |
| 5,776,184 A | 7/1998 | Tuch | 623/1 |
| 5,820,917 A | 10/1998 | Tuch | 427/2.1 |
| 5,823,996 A | 10/1998 | Sparks | 604/96 |
| 5,824,048 A | 10/1998 | Tuch | 623/1 |
| 5,833,659 A | 11/1998 | Kranys | 604/96 |
| 5,855,598 A | 1/1999 | Pinchuk | 623/1 |
| 5,865,814 A | 2/1999 | Tuch | 604/265 |
| 5,948,018 A | 9/1999 | Dereume et al. | 623/1 |
| 6,045,899 A | * 4/2000 | Wang et al. | 428/315.7 |
| 6,120,477 A | * 9/2000 | Campbell et al. | 604/96 |
| 6,447,835 B1 | * 9/2002 | Wang et al. | 427/2.24 |

* cited by examiner

*Primary Examiner*—Gregory Huson
*Assistant Examiner*—Anuradha Ramana
(74) *Attorney, Agent, or Firm*—Cameron Kerrigan; Squire Sanders & Dempsey, L.L.P.

(57) ABSTRACT

A drug delivery device for delivering therapeutic agents and method of making such a device. The device including an inflatable balloon having a plurality of holes formed in the wall of the balloon. A microporous coating covers a portion of the outer surface of the wall of the balloon. The thickness of the coating and the size of the micropores can permit controlled delivery of a substance from the micropores of the coating and into the tissue of a patient's lumen.

11 Claims, 7 Drawing Sheets

BALLOON CATHETER FOR DELIVERING THERAPEUTIC AGENTS

FIELD OF THE INVENTION

The present invention relates to a device and method of making a porous membrane. More specifically, this invention relates to a microporous membrane that can be formed on the outer surface of the inflatable member of a balloon catheter.

BACKGROUND OF THE INVENTION

A variety of surgical procedures and medical devices are currently used to relieve intraluminal constrictions caused by disease or tissue trauma. An example of one such procedure is percutaneous transluminal coronary angioplasty (PTCA). PTCA is a catheter-based technique whereby a balloon catheter is inserted into a blocked or narrowed coronary lumen of the patient. Once the balloon is positioned at the blocked lumen or target site, the balloon is inflated causing dilation of the lumen. The balloon is deflated and the catheter is then removed from the target site and the patient's lumen thereby allowing blood to freely flow through the unrestricted lumen.

Although PTCA and related procedures aid in alleviating intraluminal constrictions, such constrictions or blockages reoccur in many cases. The cause of these recurring obstructions, termed restenosis, is due to the body responding to the surgical procedure. Restenosis of the artery commonly develops over several months after the procedure, which may require another angioplasty procedure or a surgical by-pass operation. Proliferation and migration of smooth muscle cells (SMC) from the media layer of the lumen to the intima cause an excessive production of extra cellular matrices (ECM), which is believed to be one of the leading contributors to the development of restenosis. The extensive thickening of tissues narrows the lumen of the blood vessel, constricting or blocking the blood flow through the vessel.

Stents, synthetic vascular grafts or drug therapies, either alone or in combination with the PTCA procedure, are often used to reduce, or in some cases eliminate, the incidence of restenosis. The term "drug(s)," as used herein, refers to all therapeutic agents, diagnostic agents/reagents and other similar chemical/biological agents, including combinations thereof, used to treat and/or diagnose restenosis, thrombosis and related conditions. Examples of various drugs or agents commonly used include heparin, hirudin, antithrombogenic agents, steroids, ibuprofen, antimicrobials, antibiotics, tissue plasma activators, monoclonal antibodies, and antifibrosis agents.

Since the drugs are applied systemically to the patient, they are absorbed not only by the tissues at the target site, but by all areas of the body. As such, one drawback associated with the systemic application of drugs is that areas of the body not needing treatment are also affected. To provide more site-specific treatment, balloon catheters are frequently used as a means of delivering the drugs exclusively to the target site. The balloon assembly of the balloon catheter is positioned at the target site and inflated to compress the arteriosclerosis and dilate the walls of the artery. The therapeutic agent is then administered directly to the target site through small holes or apertures in the wall of the balloon assembly. The apertures through the balloon may be formed by mechanical punching, mechanical drilling, directing a laser beam at the elastic material, directing an ion beam at the elastic material, or directing an electron beam at the elastic material, among other possibilities.

Apertures formed in the walls of the balloon assembly offer many advantages to potential users. However, such devices may be deficient in their drug delivery characteristics. For example, when the balloon is filled with therapeutic or diagnostic liquids/fluids under relatively high pressure, fluid is ejected from the apertures in the form of a jet-like flow. The fluid jetting from the apertures is at such a velocity so as to cause tissue damage to the lumen or vessel wall. Since the rate at which the drug is released or delivered to the target site is a function of the structural properties of the apertures, drug release rates are inadequately controlled. As such, the balloon configuration greatly limits the usefulness of the catheter.

SUMMARY OF THE INVENTION

In view of the above, it is apparent that there is a need to provide a drug delivery device that delivers drugs, therapeutic agents, diagnostic fluids and the like deep within the tissue without causing damage to the tissue and significant systemic loss of delivered fluid materials. It is also desirable that the drug-delivery device allows one or more drugs to be released at controlled rates. There is also a need to provide a method of manufacturing such an improved drug delivery device that is convenient, efficient and cost effective.

In one embodiment of the present invention, the drug delivery device includes an elongated shaft, having a distal end and a proximal end, and an inflation assembly coupled to the distal end of the elongated shaft. The inflation assembly includes an inflatable balloon having a plurality of holes formed in the wall of the balloon. Further, a microporous coating covers a portion of the outer surface of the wall of the balloon. The thickness of the coating and the size of the micropores permit controlled delivery of a substance from the elongated shaft to the holes in the balloon and through the micropores of the coating covering the balloon.

Another aspect of the present invention is a method for making a drug delivery device. In one aspect of the invention, the method includes providing a catheter-based device having a porous inflatable member secured at a distal end of said device. A first solution and a second solution are applied onto the porous inflatable member to coat the outer surface of the porous inflatable member. The coating is then dried to produce a microporous precipitate on the outer surface of the porous inflatable member.

In general, drug(s) flow through the elongated shaft and into the inflatable member causing the inflatable member to inflate. Upon reaching a predetermined pressure, the drug(s) stream out of the holes of the inflatable member and disseminate from the pores of the microporous coating at a controlled release rate. Generally, the flow rate of fluid from the coated inflatable member is a function of the thickness and pore size of the microporous coating. As such, the microporous coating disperses the jet-like streams of liquid ejected from the holes of the inflatable member so that the fluid oozes or controllably exudes from the microporous coating to prevent the jetting effect from damaging tissue.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

FIG. 3B is a sectional view of a portion of the drug delivery device of FIG. 3a;

DETAILED DESCRIPTION OF THE INVENTION

Figure 1:
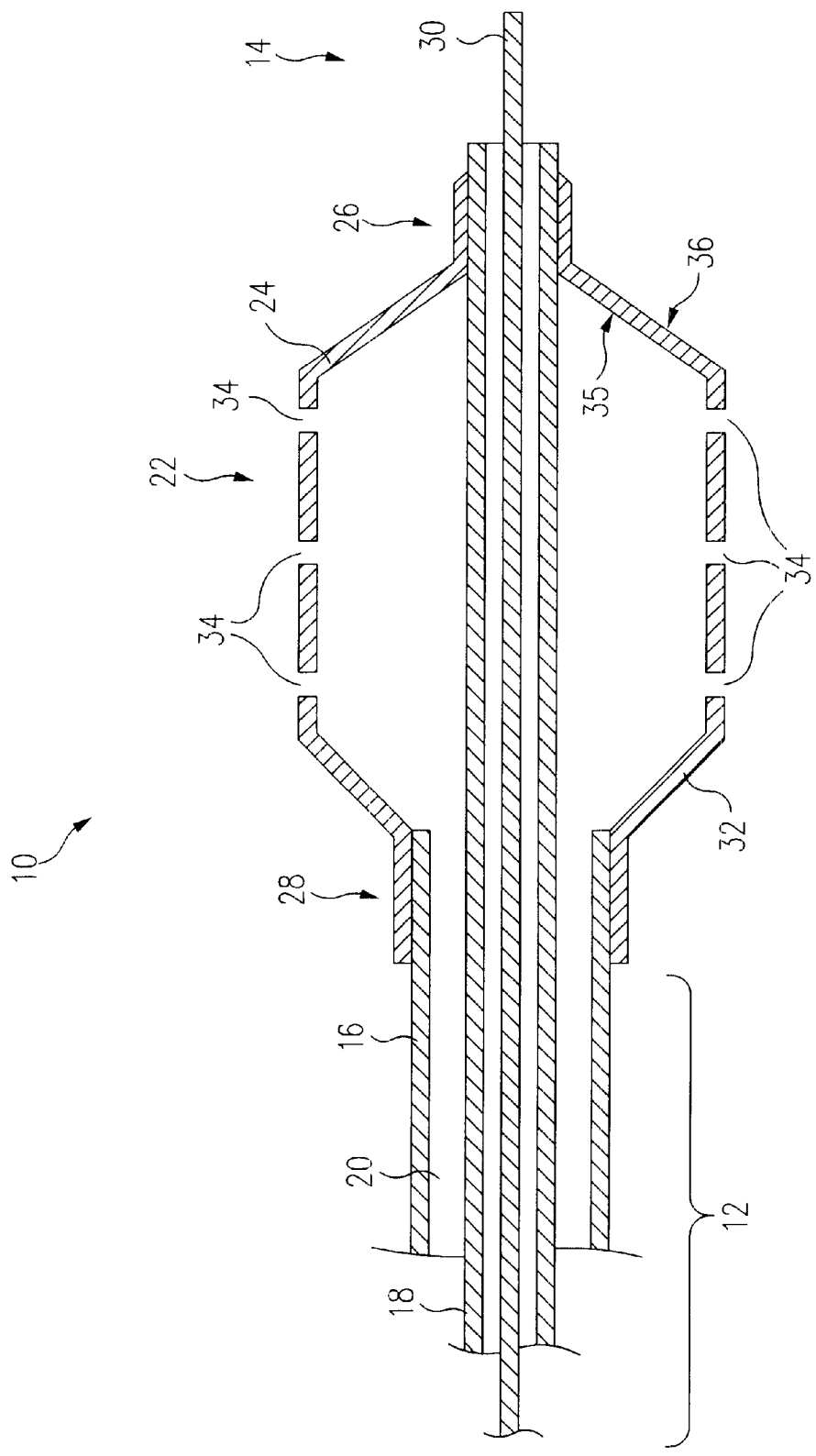
FIG. 1 is a sectional view of a drug delivery device in accordance with an embodiment of the present invention.

FIG. 1 illustrates a drug delivery device 10. For convenience and ease of comprehension, the medical device referenced in the text and figures of the present disclosure is a balloon catheter. However, it should be noted that other medical devices or prosthesis including, but not limited to, stents, stent coverings, vascular grafts, or other implantable devices, are also within the scope of the claimed invention.

As shown in FIG. 1, the catheter 10 generally comprises an elongated shaft 21 having a distal end 14 and a proximal end (not shown). In one embodiment, the catheter shaft 12 houses an outer tubular member 16, an inner tubular member 18, an annular lumen 20 extending between the inner and outer tubular members 18, 16 and an inflation assembly 22 on the distal extremity of the catheter shaft 12. The inflation assembly 22 includes a porous inflatable member or balloon 24 that is secured at its distal end 26 to the inner tubular member 18 and is secured at its proximal end 28 to the outer tubular member 16. Adhesives, welds, heat bonding or other conventional attachment devices or methods not specifically described herein can be used to secure the inflation assembly 22 to the tubular members 18, 16. For convenience and ease of comprehension, the catheter 10 referenced in the text and figures of the present disclosure is configured according to the above-described design. However, it should be noted that other catheter-based designs are also within the scope of the claimed invention.

The structural dimensions and materials of construction for the inner and outer tubular members 18, 16 can be selected from conventional materials and dimensions. Conventional methods of making the tubular members 18, 16 can also be employed. In one embodiment, inner and outer tubular members 18, 16 can be made from extruded polyethylene. However, other materials can be used, including, but not limited to, nylon, thermoplastic elastomer resins (e.g., Pebax®), PEEK (polyetheretherketone), and thermoplastic polyester elastomers (e.g., Hytrel®). The inner tubular member 18 is approximately 137 cm (53.94 inches) in length and has internal and external diameters of about $4.445 \times 10^{-2}$ cm (0.0175 inch) and $5.715 \times 10^{-2}$ cm (0.0225 inch), respectively. The approximate length and internal and external diameters of the outer tubular member 16 are 135 cm (53.15 inches), $7.112 \times 10^{-2}$ cm (0.028 inch), and 0.0864 cm (0.034 inch), respectively.

The inner tubular member 18 of the catheter 10 is configured to slidably receive a guide wire 30. The guide wire 30 extends from beyond the distal end 14 of the catheter 10 to a guide wire exit (not shown) located near the proximal end of the catheter 10. The guide wire 30 serves as the steering mechanism of the catheter 10 and enables an operator to maneuver the catheter 10 through the various vessels and lumens of the patient to the chosen target site. In one embodiment, overall length and diameter of the guide wire 30 are within the range of approximately 190 cm to 300 cm (74.8 inches to 118.1 inches) and 0.0386 cm to 0.0483 cm (0.0152 inch to 0.019 inch), respectively. The guide wire 30 may be fabricated from a variety of materials including, but not limited to, stainless steel, Nitinol™, platinum and polymers. These and other similar materials exhibit the required structural properties, such as strength and flexibility, desired in guide wire elements.

Figure 2:
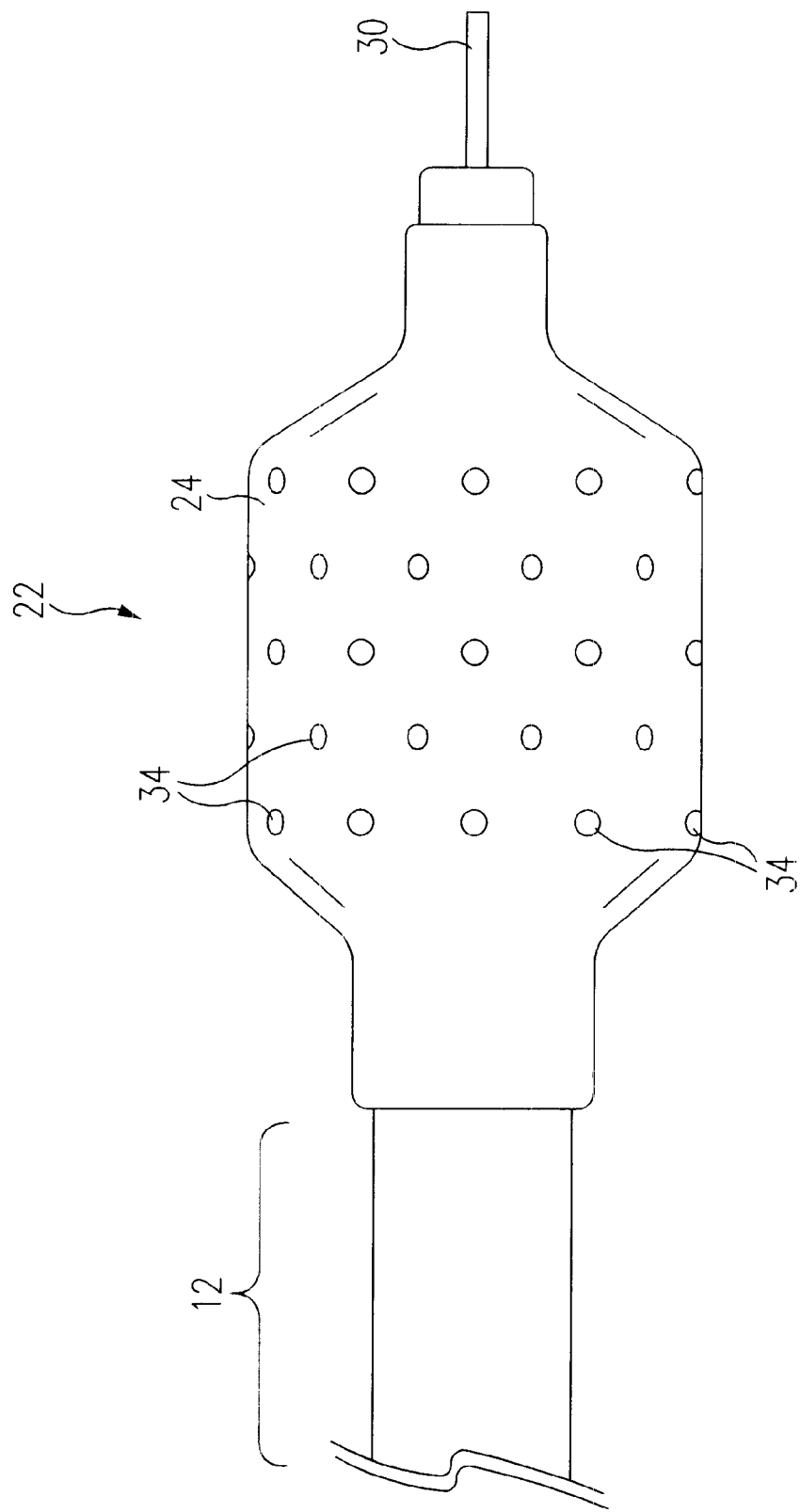
FIG. 2 is a perspective view of the drug delivery device of FIG. 1.

As shown in FIGS. 1 and 2, the inflation assembly 22 generally comprises a porous inflatable balloon 24. The inflatable balloon 24 may be used for various procedures including, but not limited to, opening narrowed passageways, distributing drugs to specific target sites, and delivering/positioning stents or other medical devices within the lumen. The term "target site," as used herein, refers to sites or tissue areas both inside and outside the lumen. During use, the inflatable balloon 24 is initially deployed in a low profile, deflated condition. When the balloon 24 is positioned at the target site, it is inflated with fluid via an inflation port (not shown) located near the proximal end of the catheter 10. During inflation of the balloon 24, fluid flows from the inflation port, through the annular lumen 20, and to the balloon 24. In addition, the fluid flows through the same lumen 20, but in the opposite direction, upon deflation and subsequent removal of the balloon 24.

The inflatable balloon 24 can be formed from any of several polymers, such as polyolefin, polyester, nylons, polyurethanes and fluoropolymers. These and other similar elastically expandable materials may be used and are available from a variety of manufacturers, examples of which include Polyester Carodel 5922C (Melinar). In one embodiment, the thickness of the wall 32 of the inflatable balloon 24 is approximately 0.00127 cm (0.0005 inch) thick. However, the wall 32 of the balloon 24 can be of any appropriate thickness provided that the thickness does not compromise properties that are important for achieving optimum performance. Such properties include high burst strength, good flexibility, high resistance to fatigue, ability to fold, ability to cross and re-cross a desired treatment area or occluded region in a body lumen, and low susceptibility to defects caused by handling, among other properties not specifically mentioned herein. As such, balloon wall thickness can be within the range of approximately 0.00127 cm (0.0005 inch) to $0.3048 \times 10^{-2}$ cm (0.0012 inch) thick.

Figure 3A:
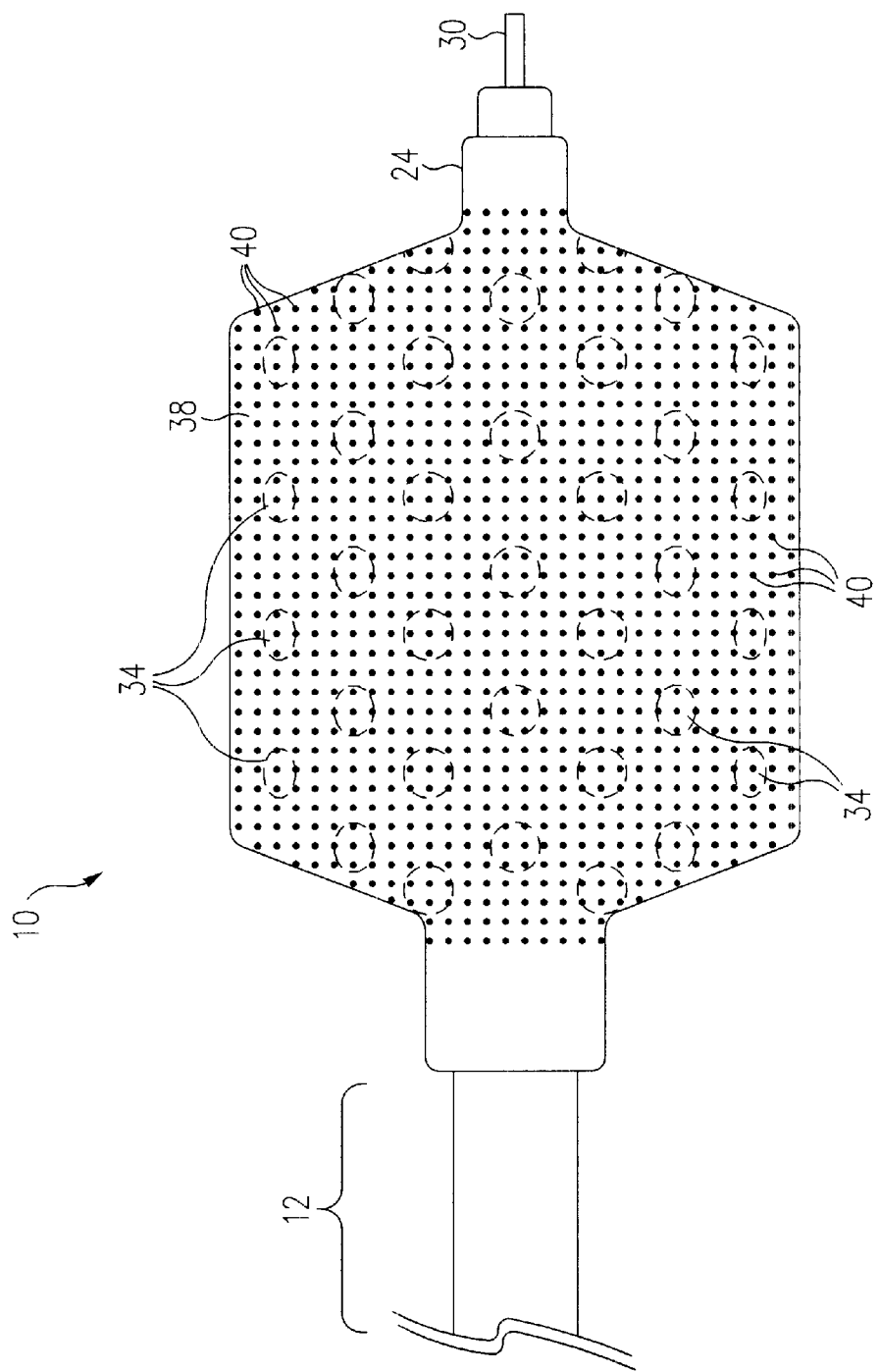
FIG. 3A illustrates an alternate perspective view of a drug delivery device in accordance with an embodiment of the present invention.
Figure 3B:
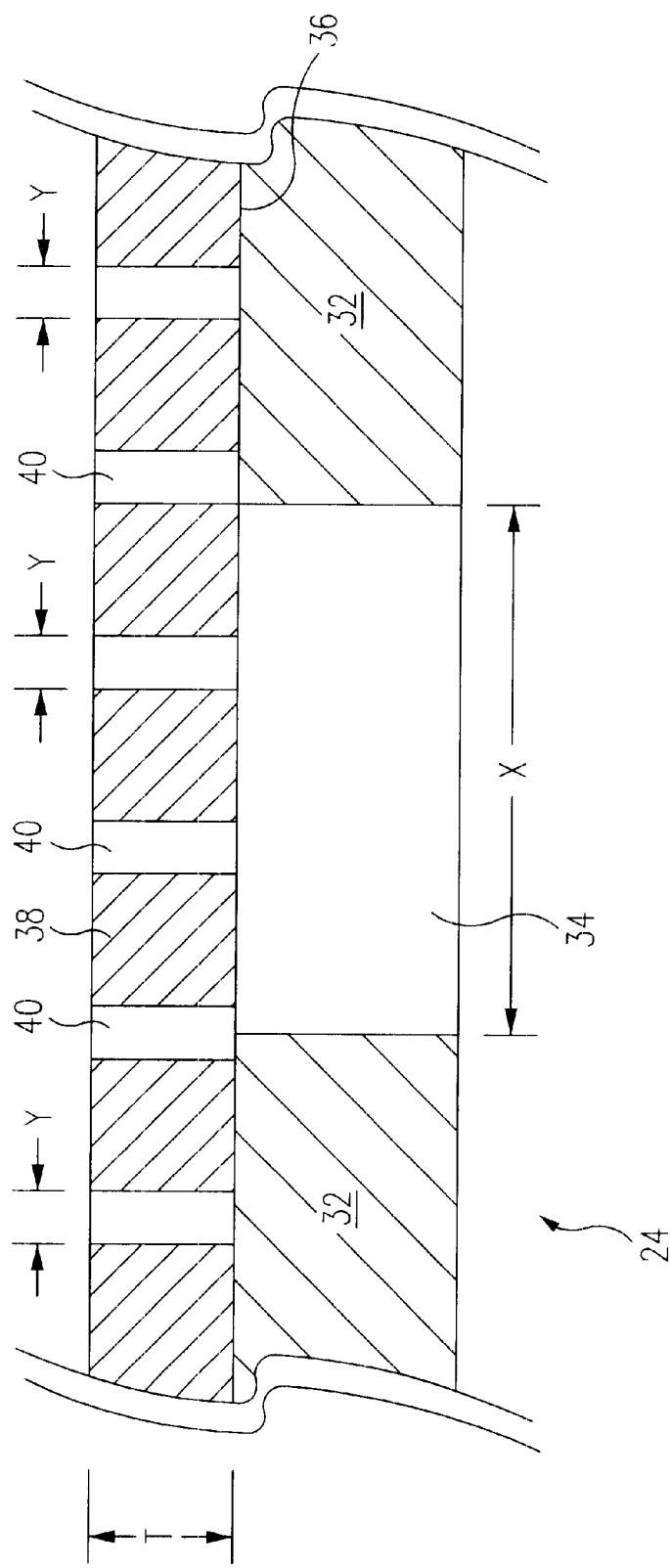

A plurality of pores or holes 34 is formed in the wall 32 of the inflatable balloon 24 and extends from the inner surface 35 through to the outer surface 36 of the wall 32. The holes 34 can be formed by laser drilling, mechanical punching, mechanical drilling, ion-bean drilling, electron beam drilling techniques or other conventional methods well known in the art. In general, the holes 34 are configured into a variety of shapes including, but not limited to, oval, circular and elliptical. As shown in FIGS. 3A and 3B, the size or diameter X of each hole 34 is approximately 0.01 mm to 0.1 mm ($3.94 \times 10^{-4}$ inch to $3.94 \times 10^{-3}$ inch) when the balloon 24 is in a inflated condition. The quantity, size and shape of the holes 34 can be varied, depending on the desired application or treatment.

The outer surface 36 of the inflatable balloon 24 is coated with one or more layers of a microporous coating or membrane 38 having a plurality of micropores 40 throughout the coating layer 38. The size or diameter Y of the pores 40 of the coating 38 ranges from approximately 0.001 mm (3.94×$10^{-5}$ inch) to 0.020 mm (7.87×$10^{-4}$ inch). The thickness T of the coating 38 is also variable from approximately 0.005 mm (1/97×$10^{-4}$ inch) to 0.020 mm (7.87×$10^{-4}$ inch). The holes 34 in the wall 32 of the inflatable balloon 24, together with the microporous coating 38 covering the outer surface 36 of the balloon 24, permit delivery of drugs radially outward from the balloon 24 and into the wall of the patient's lumen in a controlled manner.

Figure 3C:
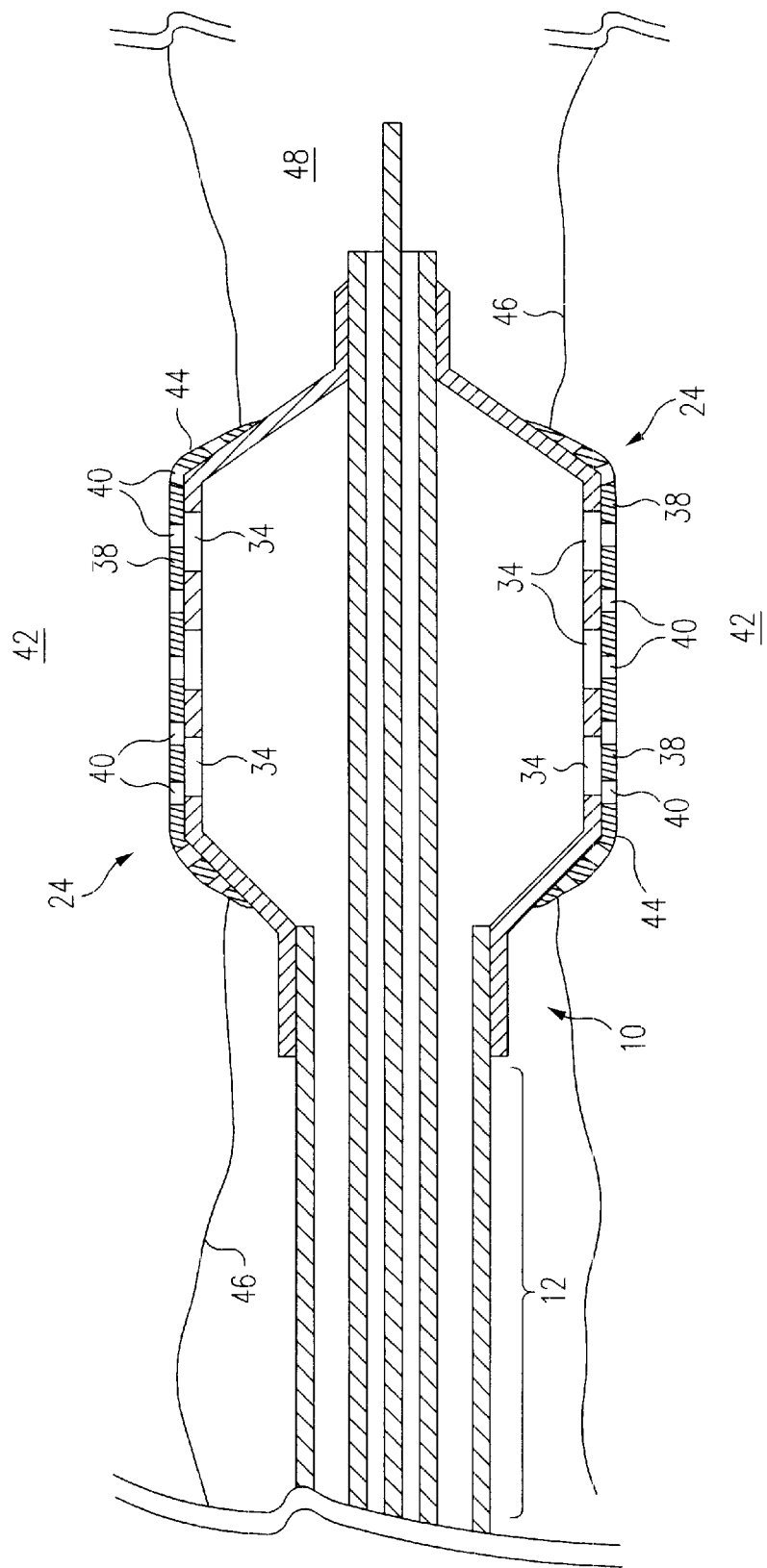
FIG. 3C is a sectional view of a drug delivery device inserted in the lumen of a patient.

As shown in FIG. 3c, when the device is positioned at the target site 42, the surface 44 of the microporous coating 38 engages the wall 46 of the patient's lumen 48. In general, drug(s) flow through the catheter shaft 12 and into the balloon 24 causing the balloon 24 to inflate. Upon reaching a predetermined pressure, the drug(s) stream out of the holes 34 of the balloon 24. Microporous coating 38 disperses the jet-like streams of liquid ejected from the holes 34 of the inflatable balloon 24 into coating 38 before the streams of liquid can contact the target site. Under the pressure of the dispersed streams of liquid, and because of the numerous pores 40, the liquid can ooze or controllably exude from microporous coating 38 and disseminates from the pores 40 at a controlled release rate. Generally, the flow rate of fluid from the coated balloon is a function of the thickness and pore size of microporous coating 38.

The terms "drug(s)," "fluid(s)," or "liquid(s)," as used herein, refers to a variety of drug classes and therapeutic substances may be used in accordance with the present disclosure. For example, therapeutic substances or agents may include, but are not limited to, antineoplastic, antimitotic, anti-inflammatory, antiplatelet, anticoagulant, anti fibrin, antithrombin, antiproliferative, antibiotic, antioxidant, and antiallergic substances as well as combinations thereof. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, actinomycin-D, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelct membrane receptor antagonist antibody, recombinant hirudin, and thrombin inhibitors such as Angiomax™ (Biogen, Inc., Cambridge, Mass.) Examples of such cytostatic or antiprolifcrative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, and dexamethasone.

While the above listed substances or agents are well known for preventative and therapeutic utility, the substances are listed by way of example and are not meant to be limiting. Other therapeutic substances which are currently available or that may be developed in the future are equally applicable. The treatment of patients using the above mentioned medicines is well-known to those of ordinary skill in the art.

The microporous coating 38 formed on the outer surface 36 of the inflatable balloon 24 can be made according to phase inversion precipitation techniques using a variety of materials. For example, silicones, polyesters or polyurethanes dissolved in tetrahydro-furan (THF), dimethylacetamide, dimethylformamide, dimethylsuylfoxide or dioxane, or other mixtures of solvents can be used. Non-solvents, such as water, can also be used during preparation of the unstable polymer coating solution.

Phase inversion precipitation techniques are well known in the manufacture of microporous membranes. In general, according to this technique, a solution of a polymer is prepared in a mixture of two miscible solvents. One of the two solvents is a poorer solvent for the polymer and less volatile than the other solvent. The solution is selectively coated onto the device 10 according to one of several coating methods, such as dipping, spraying, etc. Once the device 10 is properly coated, the solution is allowed to air dry at 40° C. and dry over-night in a vacuum chamber. During the drying phase of the solution, the better solvent evaporates more rapidly than the poorer solvent, causing the polymer to form a precipitant out of the solution. After the solution is completely dried, an open porous structure (i.e. the precipitant) remains and covers the selected areas of the device 10. The size of the resultant pores is determined by the nature of the ingredients (i.e. polymers, solvents, non-solvents) and relative concentrations of the ingredients chosen.

Microporous Coating Techniques

To aid in the treatment of various conditions affecting a body lumen, the outer surface 36 of the porous, inflatable balloon 24 of a catheter 10 is coated with a microporolis membrane 38. Various methods can be employed to coat the inflatable balloon 24. The following examples illustrate various microporous coating techniques, but do not limit possible techniques within the scope of the present invention.

EXAMPLE 1

The inflatable member 24 of a balloon catheter 10 having a plurality of holes 34 formed in the wall 32 of the 30 mm by 20 mm (1.18 inch by 0.79 inch) balloon 24 is suspended from a fixture (not shown) and partially inflated. In one embodiment, approximately 6.9 kPa–13.8 kPa (approximately 1–2 psi) of air flows from the inflation port (not shown), through the annular lumen 20, and into the inflatable balloon 24 causing the balloon 24 to partially inflate. Other fluids, such as nitrogen, at variable pressures, ranging from about 6.9 kPa–13.8 kPa (about 1 psi to 2 psi), can also be used to inflate the balloon 24. In general, the desired fluid pressure flowing through the balloon should be an amount that allows partial inflation of the balloon 24 while maintaining the structural integrity of the microporous coating 38.

Figure 4:
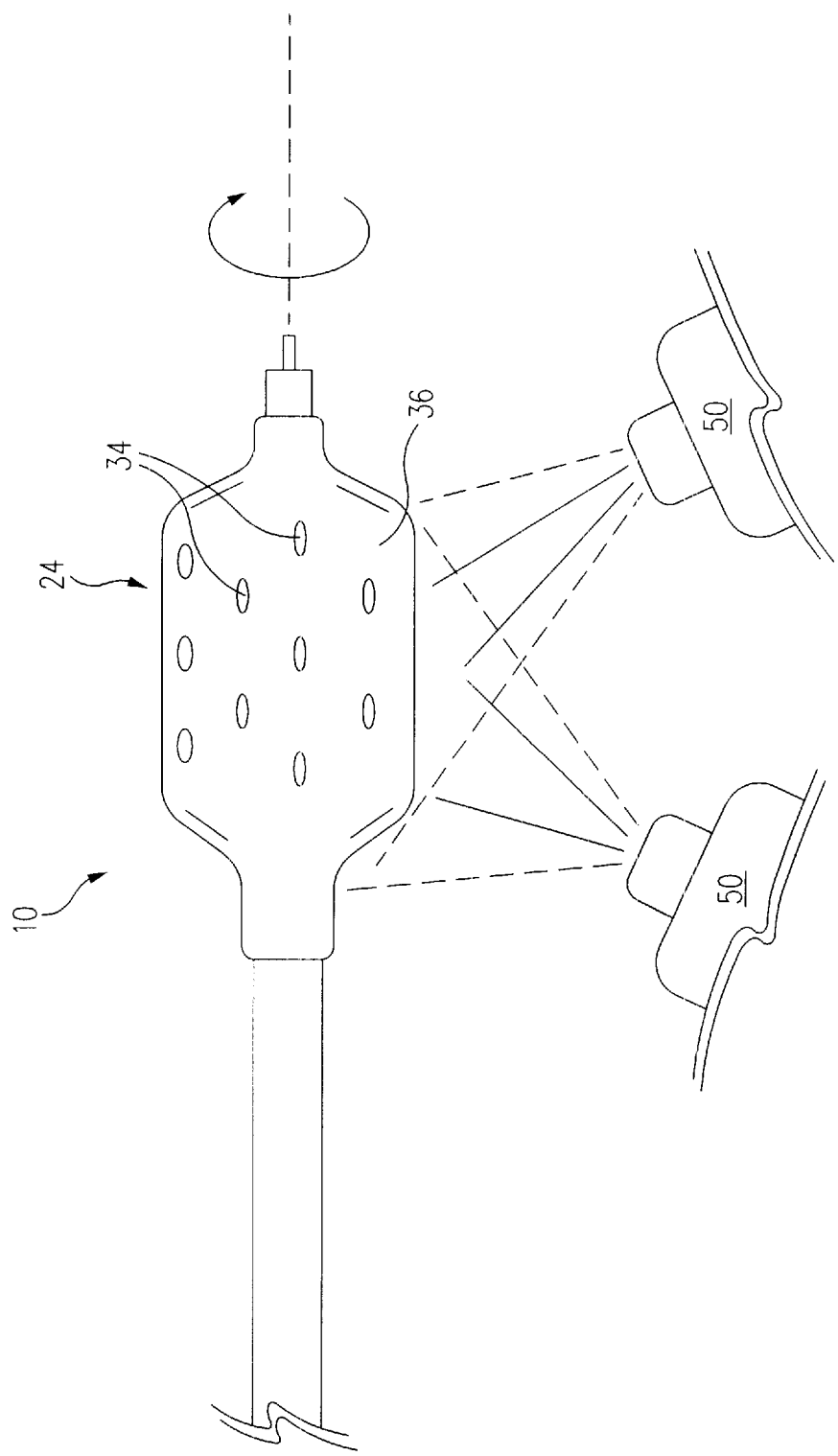
FIG. 4 illustrates a perspective view of an embodiment of applying a coating to a drug delivery device in a partially inflated configuration.

A first solution, i.e. polymer solution, is formulated using 1% w/w Tecoflex RTM EF-600 (Termedica, Inc.) dissolved in THF/1.4 Dioxane mixture (2:1). Note that "w/w" is an abbreviation for "by weight," used in chemistry and pharmacology to describe the concentration of a substance in a mixture or solution. For example, 25% w/w means that the mass of the substance is 25% of the total mass of the solution or mixture. As shown in FIG. 4, the balloon catheter 10 is rotated about its axis while maintaining the balloon 24 in its partially inflated configuration. The polymer solution and a second solution, or non-solvent (i.e. water), are simultaneously but separately sprayed from two spray guns 50 (Badger Airbrush #250-2) at about the same volumetric flux onto the outer surface 36 of the rotating partially-inflated balloon 24. In one embodiment, the polymer solution and non-solvent are sprayed at a volumetric flux of between about 1–5.0 ml/min at nitrogen pressure of about 103 kPa (15 psi). However, volumetric flux of the polymer solution and non-solvent may vary based upon polymer type, solvent characteristics, non-solvent characteristics, balloon size, desired flow rate; desired coating thickness and pore size, etc.

After the outer surface 36 of the balloon 24 is spray coated with the mixture, the coating 38 (not shown) is allowed to air dry for approximately 4 hours at 40 ° C., with the balloon partially inflated. The balloon catheter 10 is then transferred to a vacuum drying oven for overnight drying (i.e. approximately 12 hours). After the coating 38 is completely dry, the above process can be repeated until the desired coated balloon characteristics are achieved.

EXAMPLE 2

Figure 5:
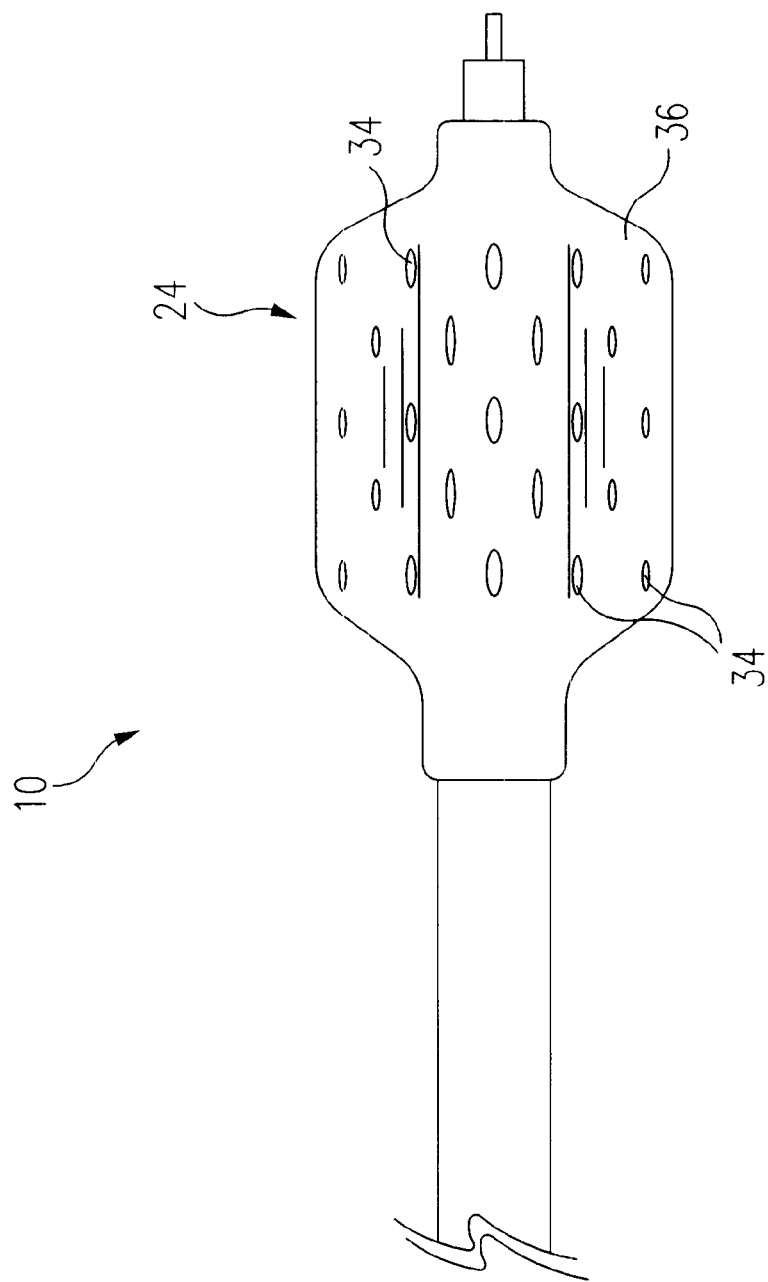
FIG. 5 illustrates an alternate perspective view of the drug delivery device in a deflated configuration.

The inflatable member 24 of a balloon catheter 10 having a plurality of holes 34 formed in the wall 32 of a 30 mm by 20 mm (1.18 inch by 0.79 inch) balloon 24 is completely deflated to a flattened configuration, as shown in FIG. 5. A first solution, i.e. polymer solution, is formulated using 1% w/w Tecoflex RTM EF-600 (Termedica, Inc.) dissolved in THF/1.4 Dioxane mixture (2:1). The polymer solution and a second solution, or non-solvent such as water, are carefully mixed to avoid precipitation during the mixing process. In one embodiment, the concentration/ratio of polymer solution to non-solvent is approximately 90:10. A coating or layer of the mixture is then applied to the balloon 24 via dipping, spraying or other appropriate application techniques. The total volume of the mixture contained in each layer depends on the desired balloon configuration. In one embodiment, a coating thickness of 0.01 mm ($3.94 \times 10^{-4}$ inch) is applied to the 30 mm by 20 mm (1.18 inch by 0.79 inch) balloon 24.

After the outer surface 36 of the balloon 24 is coated with the mixture, the coating 38 (not shown) is allowed to air dry for approximately 4 hours at 40° C. The balloon catheter 10 is then further dried in a vacuum drying oven at about 40° C. for approximately 12 hours. After the coating 38 is completely dry, the above process can be repeated until the desired coated balloon characteristics are achieved.

The above-described coating examples are specific to assembled balloon catheters 10. However, in an alternate embodiment, the above described fabrication processes can also be performed on the inflatable member 24 prior to its assembly on the catheter shaft 12. In addition, alternative methods of applying a microporous coating 38 onto the surface 36 of the inflatable member 24 of a balloon catheter 10, including various combinations of methods, are also within the scope of the present disclosure. Further, by modifying the ingredients (i.e. types and concentrations of polymers, solvents and non-solvents), pores 40 of varying sizes and quantities may be formed. For example, in one embodiment, a single layer of coating 38 having smaller and more numerous pores 40 may be preferred to control drug release rates/duration. In an alternate embodiment, several layers of a coating 38, whereby each layer is made of the same ingredients, may be applied to achieve the desired fluid flow rate characteristics. In yet another embodiment, each layer of coating 38 applied to the balloon 24 is made of different ingredients, thereby providing alternative fluid flow rate characteristics.

Although not specifically described, the scope of the present invention also includes alternative coated balloon embodiments having various combinations of ingredients and layering patterns/methods. The particular coating ingredient(s) and layering patterns applied to the balloon 24 are configured according to the requirements of the desired treatment or diagnosis.

Although the invention has been described in terms of particular embodiments and applications, one of ordinary skill in the art, in light of this teaching, can generate additional embodiments and modifications without departing from the scope of the claimed invention. Accordingly, it is to be understood that the drawings and descriptions herein are proffered by way of example to facilitate comprehension of the invention and should not be construed to limit the scope thereof.

What is claimed is:

1. A drug delivery device, comprising:

an elongated shaft having a distal section and a proximal section;

an inflation assembly coupled to said distal section of said elongated shaft, said inflation assembly including an inflatable balloon having a plurality of holes defined in a wall of said balloon; and a microporous precipitate coating, wherein a majority of the inner surface of said microporous precipitate coating is in intimate contact with a majority of the outer surface of said balloon wall so as not to include a gap between said microporous precipitate coating and said balloon wall, and wherein said microporous precipitate coating has micropores of a size that permit controlled delivery of a drug from said elongated shaft to said holes in said balloon and through said micropores of said microporous precipitate coating disposed on the outer surface of said balloon wall.

2. The device of claim 1, wherein said holes are laser drilled with a diameter in a range from approximately 0.01 mm to 0.1 mm ($3.94 \times 10^{-4}$ inch to $3.94 \times 10^{-3}$ inch).

3. The device of claim 1, wherein said size of said micropores is in a range from approximately 0.001 mm ($3.94 \times 10^{-5}$ inch) to 0.020 mm ($7.87 \times 10^{-4}$ inch).

4. The device of claim 1, wherein a thickness of said microporous precipitate coating is in a range from approximately 0.005 mm ($1/97 \times 10^{-4}$ inch) to 0.020 mm ($7.87 \times 10^{-4}$ inch).

5. The device of claim 1, wherein said microporous precipitate coating is made using phase inversion precipitation techniques.

6. The device of claim 1, wherein said microporous precipitate coating is formed from a polymer, a solvent and a non-solvent.

7. The device of claim 6, wherein said polymer is taken from the group consisting of silicones, polyesters and polyurethanes.

8. The device of claim 6, wherein said solvent is taken from the group consisting of: tetrahydrofuran (THF), dimethylacetamide, dimethylformamide, dimethylsulfoxide and dioxane.

9. The device of claim 6, wherein said non-solvent is water.

10. The device of claim 1, wherein said drug is taken from the group consisting of: antithrombotics, antiproliferatives, anti-inflammatory agents, smooth muscle cell migration inhibitors, reendothelialization agents and restenosis-reducing drugs.

11. A drug delivery system comprising:

a catheter having a distal section and a proximal section;

an inflatable balloon integrated with said distal section of said catheter, said balloon having a plurality of holes for delivering a drug to a body vessel; and a microporous precipitate of a polymer disposed on a portion of the surface of said balloon, said precipitate covering at least a portion of said holes and having micropores of a size that permit controlled delivery of a drug from said holes to said body vessel.

* * * * *